US006448052B2

(12) United States Patent
Yasohara et al.

(10) Patent No.: US 6,448,052 B2
(45) Date of Patent: Sep. 10, 2002

(54) CARBONYL REDUCTASE ENZYME AND METHODS FOR ITS USE

(75) Inventors: Yoshihiko Yasohara, Himeji; Noriyuki Kizaki, Takasago; Junzo Hasegawa, Akaski; Masaru Wada, Kyoto; Sakayu Shimizu, Kyoto; Michihiko Kataoka, Kyoto; Kazuhiko Yamamoto, Takatsuki; Hiroshi Kawabata, Kyoto; Keiko Kita, Tottori, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/777,157

(22) Filed: Feb. 5, 2001

Related U.S. Application Data

(62) Division of application No. 09/367,012, filed on Nov. 24, 1999, now Pat. No. 6,218,156.

(30) Foreign Application Priority Data

Feb. 7, 1997 (JP) .............................................. 9-025667
Apr. 30, 1997 (JP) .............................................. 9-113052

(51) Int. Cl.[7] .............................. C12P 7/62; C12N 9/04
(52) U.S. Cl. ....................................... 435/135; 435/190
(58) Field of Search .................................. 435/135, 190

(56) References Cited

FOREIGN PATENT DOCUMENTS

| JP | 61146191 A | 7/1986 |
|----|------------|--------|
| JP | 63304991 A | 12/1988 |
| JP | 06038776 A | 2/1994 |
| JP | 06209782 A | 8/1994 |
| JP | 08336393 A | 12/1996 |

OTHER PUBLICATIONS

Peters, J., et al. (1992) Appl Microbiol. Biotechnol. 38, 334–340.*
Peters, J., et al. (1993) Tetrahedron Assymmetry 4(7), 1683–1692.*
Peters, J., et al. (1993) Biocatalysis 8, 31–46.*
Japanese Search Report dated Sep. 1, 1997.
Peters, Jorg et al., A Novel NADH–Dependent Cabonyl Reductase with an Extremely Broad Substrate Range from Candida Parapsilosis: Purification and Characterization, Enzyme Microb. Technol., vol. 15, Nov., pp. 950–958, 1993.
Patel, Ramesh et al., Stereoselective Reduction of β–keto Esters by Geotrichum Candidum, Enzyme Microb. Technol., vol. 14, Sep., pp. 731–738, 1992.

* cited by examiner

*Primary Examiner*—Charles L. Patterson, Jr.
(74) *Attorney, Agent, or Firm*—Howrey Simon Arnold & White, LLP

(57) ABSTRACT

An enzyme having carbonyl reduction activity of reducing a carbonyl compound asymmetrically to produce an optically active alcohol, a DNA coding the enzyme, a plasmid having the DNA, a transformant which is a cell transformed with the plasmid, and a production method of an optically active alcohol using the enzyme and/or the transformed cell are provided.

14 Claims, 4 Drawing Sheets

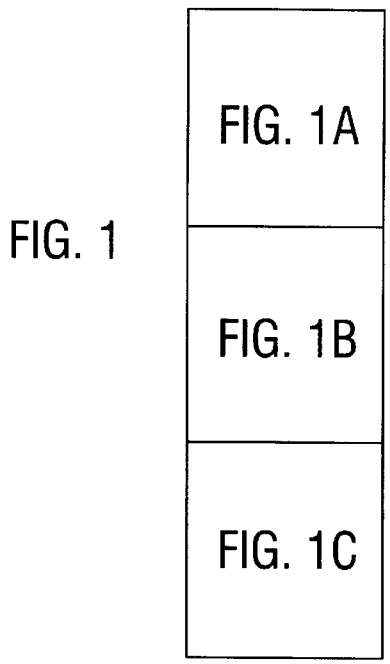

```
AAGCTTGGGGAACCGACGTCCCCGCCCTCGTACATGCAGTGCAT     44

ACAGCATTGCCCAAACCCCACATTGTGCCCCCACCCCCCGCGGA     89

TTCCGTAACTATATAAAGGCCGCCAGTGCCGACTATGGACCATCA    134

TCCCGAAATCACCAAGAACTAACAATGGCTAAGAACTTCTCCAAC    179
                          MetAlaLysAsnPheSerAsn

GTCGAGTACCCCGCCCCGCCTCCGGCCCACACCAAGAACGAGTCG    224
ValGluTyrProAlaProProProAlaHisThrLysAsnGluSer

CTGCAGGTCCTTGACCTGTTCAAGCTGAATGGCAAGGTTGCCAGC    269
LeuGlnValLeuAspLeuPheLysLeuAsnGlyLysValAlaSer
```

FIG. 1A

```
ATCACTGGCTCGTCCAGCGGTATTGGCTACGCTCTGGCTGAGGCC          314
IleThrGlySerSerSerGlyIleGlyTyrAlaLeuAlaGluAla

TTCGCGCAGGTCGGCGCTGACGTCGCCATCTGGTACAACAGCCAC          359
PheAlaGlnValGlyAlaAspValAlaIleTrpTyrAsnSerHis

GACGCTACTGGCAAGGCTGAGGCCCTCGCCAAGAAGTACGGCGTC          404
AspAlaThrGlyLysAlaGluAlaLeuAlaLysLysTyrGlyVal

AAGGTCAAGGCCTACAAGGCGAACGTGAGCAGCTCTGACGCCGTG          449
LysValLysAlaTyrLysAlaAsnValSerSerSerAspAlaVal

AAGCAGACGATCGAGCAGCAGATCAAGGACTTCGGCCACCTCGAC          494
LysGlnThrIleGluGlnGlnIleLysAspPheGlyHisLeuAsp

ATTGTCGTGGCGAACGCCGGCATTCCCTGGACGAAGGGTGCCTAC          539
IleValValAlaAsnAlaGlyIleProTrpThrLysGlyAlaTyr

ATCGACCAGGACGACGACAAGCACTTCGACCAGGTCGTTGACGTC          584
IleAspGlnAspAspAspLysHisPheAspGlnValValAspVal

GATCTGAAGGGTGTTGGATACGTCGCGAAGCACGCTGGCCGTCAC          629
AspLeuLysGlyValGlyTyrValAlaLysHisAlaGlyArgHis

TTCCGCGAGCGCTTCGAGAAGGAGGGCAAGAAGGGCGCCCTTGTG          674
PheArgGluArgPheGluLysGluGlyLysLysGlyAlaLeuVal

TTCACGGCCTCCATGTCTGGCCACATTGTGAACGTGCCCCAGTTC          719
PheThrAlaSerMetSerGlyHisIleValAsnValProGlnPhe

CAGGCCACGTACAACGCGGCCAAGGCTGGCGTGCGCCACTTCGCG          764
GlnAlaThrTyrAsnAlaAlaLysAlaGlyValArgHisPheAla
```

FIG. 1B

```
AAGTCGCTGGCCGTCGAGTTCGCGCCGTTCGCGCGCGTGAACTCT             809
LysSerLeuAlaValGluPheAlaProPheAlaArgValAsnSer

GTGTCGCCGGGCTACATCAACACGGAGATCTCGGACTTCGTGCCC             854
ValSerProGlyTyrIleAsnThrGluIleSerAspPheValPro

CAGGAGACGCAGAACAAGTGGTGGTCGCTCGTGCCCCTTGGCCGC             899
GlnGluThrGlnAsnLysTrpTrpSerLeuValProLeuGlyArg

GGCGGAGAGACGGCCGAGCTCGTTGGCGCCTACCTGTTCCTTGCA             944
GlyGlyGluThrAlaGluLeuValGlyAlaTyrLeuPheLeuAla

TCTGACGCCGGCTCGTACGCCACTGGTACGGACATCATTGTTGAC             989
SerAspAlaGlySerTyrAlaThrGlyThrAspIleIleValAsp

GGTGGCTACACGCTTCCCTAAGCGGCGTGCCGAAAACATAGAGCT            1034
GlyGlyTyrThrLeuPro***

ATCTATATAACCATAATGATGCGCATATTATGATCTACTACTTTG            1079

ACTTCGATCGGAACTTAGGAACGATAAGGGTGGAATGCGTGAAAG            1124

CGTGCATGCTGCAGAGCGGTGTAATCGGCAGGGCTGTAGGGTGCC            1169

TGAGGCGGCGGGCCAGCAGTGCATGTAACCGGAGCTGAAGCGGAG            1214

GCACACATTGCGATGCAGCGAAGCACGGCCGCCAGAACTCTTTGA            1259

GAACAAGCGCGGCCCTCGACTATGCAGCGGCAACAAGCGAATTC             1303
```

CARBONYL REDUCTASE ENZYME AND METHODS FOR ITS USE

This is a divisional application of co-pending application Ser. No. 09/367,012, filed Nov. 24, 1999 now U.S. Pat. No. 6,218,156.

TECHNICAL FIELD

The present invention relates to an enzyme having carbonyl reduction activity of reducing a carbonyl compound asymmetrically to produce an optically active alcohol (hereafter, such an enzyme is referred to as a CRD enzyme), a DNA coding such an enzyme, a plasmid having such a DNA, a transformant which is a cell transformed with such a plasmid, and a production method of an optically active alcohol using the enzyme and/or the transformed cell. The resultant optically active alcohol, for example, (S)-4-halo-3-hydroxy butyric ester, is a useful compound as a raw material for the synthesis of medicines, agricultural chemicals, and the like.

BACKGROUND ART

A number of CRD enzymes are known (see Yuki Gosei Kagaku, 49, 52 (1991) and Eur. J. Biochem., 184, 1 (1981)). Among such CRD enzymes, those which act on 4-halo acetoacetic ester to produce (S)-4-halo-3-hydroxy butyric ester, which are derived from microbes, and which have reported characteristics, are only a *Geotrichum candidum* derived enzyme (Enzyme Microb. Technol. (1992), Vol. 14, 731) and a *Candida parapsilosis* derived enzyme (Enzyme Microb. Technol. (1993), Vol. 15, 950). However, no information has been reported on genes coding these two types of enzymes. The reduction of 4-halo acetoacetic ester using such enzymes only proceeds at a low substrate concentration. It is therefore impractical to synthesize (S)-4-halo-3-hydroxy butyric ester using such enzymes as catalysts.

Besides the above reaction using the two types of enzymes, a number of reactions using microbe bodies and the products of such reactions are known to realize asymmetric reduction of 4-halo acetoacetic ester (Japanese Patent No. 1723728, Japanese Laid-Open Publication Nos. 6-209782 and 6-38776, etc.) However, such reactions are not performed at a high substrate concentration, and thus it cannot be asserted that a practical production method has been established. See, for example, a reaction method using a two-phase system with an organic solvent (Japanese Patent No. 2566962). A method using a ruthenium-optically active phosphine complex as a catalyst has also been reported (Japanese Laid-Open Publication No. 1-211551). This method however has many problems to be solved, such as the requirement of a high-pressure reaction vessel and need for an expensive catalyst.

Under the above circumstances, development of a practical enzyme has been desired for use in asymmetric reduction of a carbonyl compound such as 4-halo acetoacetic ester to produce an optically active alcohol such as (S)-4-halo-3-hydroxy butyric ester.

A CRD enzyme requires a reduction-type coenzyme for reaction. Conventionally, when a carbonyl compound is to be reduced using a microbe body and the like having a CRD enzyme, a saccharide such as glucose is added to a reaction system to activate a group of regeneration-system enzymes for changing an oxidized coenzyme to a reduced type, thereby regenerating the coenzyme so as to be used for the reduction. Such a group of regeneration-system enzymes are likely to be blocked or damaged by substrates and reduced products. This has been considered to be one of major reasons why the reduction proceeds only when the concentration of substrates or products is low. It is known that the amount of an expensive coenzyme used during reduction can be greatly reduced by combining an enzyme having the ability of regenerating a coenzyme on which a CRD enzyme depends with the CRD enzyme during the reaction (Japanese Patent No. 2566960 and Enzyme Microb. Technol. (1993), Vol. 15, 950, for example). In this case, however, it is required to prepare an enzyme source for regenerating the coenzyme separately from the preparation of the CRD enzyme before the regenerating enzyme is added to a reaction system.

The Inventors of the present application have discovered a novel Candida-genus derived CRD enzyme, and found that an optically active alcohol can be efficiently produced from a carbonyl compound by using this CRD enzyme.

Also found is that an optically active alcohol can be efficiently produced by using a transformed cell containing a gene of an enzyme having the ability of regenerating a coenzyme (e.g., a glucose dehydrogenase gene) concurrently.

Thus, the present invention to be described in the specification can advantageously provide a novel CRD enzyme, a DNA coding this enzyme, a plasmid having this DNA, a transformant which is a cell transformed with this plasmid, and a production method of an optically active alcohol using the above enzyme and/or transformed cell.

DISCLOSURE OF THE INVENTION

The carbonyl reductase according to the present invention has physical and chemical properties (1) to (4) of:

(1) action:

acting on ethyl 4-chloroacetoacetate using NADPH as a coenzyme to produce ethyl (S)-4-chloro-3-hydroxybutyrate;

(2) substrate specificity:

exhibiting a strong activity to ethyl 4-chloroacetoacetate while exhibiting substantially no activity to ethyl acetoacetate;

(3) optimal pH: 5.5 to 6.5; and (4) action optimal temperature: 50° C. to 55° C.

In one embodiment, the carbonyl reductase has additional physical and chemical properties (5) to (7) of:

(5) heat stability: being stable up to about 40° C. when processed at pH 7.0 for 30 minutes;

(6) inhibitor: being inhibited by mercury ions and quercetin; and (7) molecular weight: about 76,000 by gel filtration analysis and about 32,000 by SDS polyacrylamide electrophoresis analysis.

The carbonyl reductase according to the present invention has an amino acid sequence of SEQ ID NO:1 of the Sequence Listing or an amino acid sequence with one or several amino acids being deleted, substituted, or added in the amino acid sequence of SEQ ID NO:1 of the Sequence Listing, or part of the amino acid sequences of SEQ ID NO:1 of the Sequence Listing, and having an activity of reducing ethyl 4-chloroacetoacetate asymmetrically to produce ethyl (S)-4-chloro-3-hydroxybutyrate.

In one embodiment, the enzyme is obtained from a microbe belonging to genus Candida. In a preferred embodiment, the enzyme is obtained from *Candida magnoliae*. In a more preferred embodiment, the enzyme is obtained from *Candida magnoliae* IFO 0705.

The DNA according to the present invention codes for the above enzyme. In one embodiment, the DNA has a nucleotide sequence of SEQ ID NO:2 of the Sequence Listing.

The plasmid according to the present invention has the above DNA sequence. In one embodiment, the plasmid is pNTS1.

The transformed cell according to the present invention is a transformant which is a cell transformed with the above plasmid. In one embodiment, the transformed cell is E. coli. In a preferred embodiment, the transformed cell is *E.coli* HB101 (pNTS1).

The plasmid according to the present invention has a DNA coding for an enzyme having an activity of asymmetrically reducing ethyl 4-chloroacetoacetate to produce ethyl (S)-4-chloro-3-hydroxybutyrate and a DNA coding for an enzyme having an ability of regenerating a coenzyme on which the enzyme depends (e.g., glucose dehydrogenase).

In one embodiment, the glucose dehydrogenase is derived from *Bacillus megaterium*. In a preferred embodiment, the plasmid is pNTS1G.

The transformed cell according to the present invention is a transformant which is a cell transformed with the above plasmid.

In one embodiment, the transformed cell is *E.coli*. In a preferred embodiment, the transformed cell is *E.coli* HB101 (pNTS1).

The transformed cell according to the present invention is a transformant which is a cell transformed with a first plasmid having a DNA coding for an enzyme having an activity of asymmetrically reducing ethyl 4-chloroacetoacetate to produce ethyl (S)-4-chloro-3-hydroxybutyrate, and a second plasmid having a DNA coding an enzyme having an ability of regenerating a coenzyme on which the enzyme depends (e.g., glucose dehydrogenase).

In one embodiment, the transformed cell is a transformant which is a cell transformed with plasmid pNTS1 and a plasmid having a DNA coding for glucose dehydrogenase derived from *Bacillus megaterium*. In a preferred embodiment, the transformed cell is *E. coli*.

The production method for producing an optically active 3-hydroxy butyric ester according to the present invention includes the steps of: reacting with a 3-oxo-butyric ester an enzyme having an activity of asymmetrically reducing a 3-oxo-butyric ester to produce an optically active 3-hydroxy-butyric ester or a culture of a microbe having an ability of producing the enzyme or a processed product of the culture; and harvesting a produced optically active 3-hydroxy-butyric ester.

The production method for producing an optically active 3-hydroxy butyric ester according to the present invention includes the steps of: reacting a transformant which is a cell transformed with a plasmid having a DNA coding for an enzyme having an activity of asymmetrically reducing a 3-oxo-butyric ester to produce an optically active 3-hydroxy-butyric ester with a 3-oxo-butyric ester; and harvesting a produced optically active 3-hydroxy-butyric ester.

The production method for producing an optically active alcohol according to the present invention includes the steps of: reacting with a carbonyl compound a transformant which is a cell transformed with a plasmid having a DNA coding for an enzyme having an activity of asymmetrically reducing a carbonyl compound to produce an optically active alcohol and a DNA coding an enzyme having an ability of regenerating a coenzyme on which the enzyme depends; and harvesting a produced optically active alcohol.

The production method of an optically active alcohol according to the present invention includes the steps of: reacting with a carbonyl compound a transformant which is a cell transformed with a first plasmid having a DNA coding for an enzyme having an activity of asymmetrically reducing a carbonyl compound to produce an optically active alcohol and a second plasmid having a DNA coding for an enzyme having an ability of regenerating a coenzyme on which the enzyme depends; and harvesting a produced optically active alcohol.

In one embodiment, the carbonyl compound is a 3-oxo-butyric ester represented by a general formula:

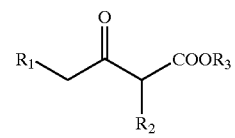

and the resultant optically active alcohol is an optically active 3-hydroxy-butyric ester represented by a general formula:

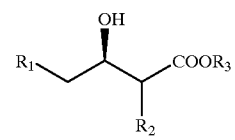

In a preferred embodiment, in the above general formulae, $R_1$ and $R_2$ are independently halogen, azide, benzyl amino, or hydrogen, one of $R_1$ and $R_2$ being hydrogen, and $R_3$ is a substituted or non-substituted alkyl group or aryl group.

In a more preferred embodiment, in the above general formulae, $R_1$ is chlorine, $R_2$ is hydrogen, and $R_3$ is ethyl.

In a preferred embodiment, in the above general formulae, $R_1$ and $R_2$ are independently an alkyl group, a hydroxyl group, or hydrogen, one of $R_1$ and $R_2$ being hydrogen, and $R_3$ is a substituted or non-substituted alkyl group or aryl group.

In a more preferred embodiment, in the above general formulae, $R_1$ is a hydroxyl group, $R_2$ is hydrogen, and $R_3$ is ethyl.

BRIEF DESCRIPTION OF THE DRAWINGS

FIG. 1 is a view showing a base sequence (SEQ ID NO:8) and an estimated amino acid sequence (SEQ ID NO:1).

BEST MODE FOR CARRYING OUT THE INVENTION

Figure 2:
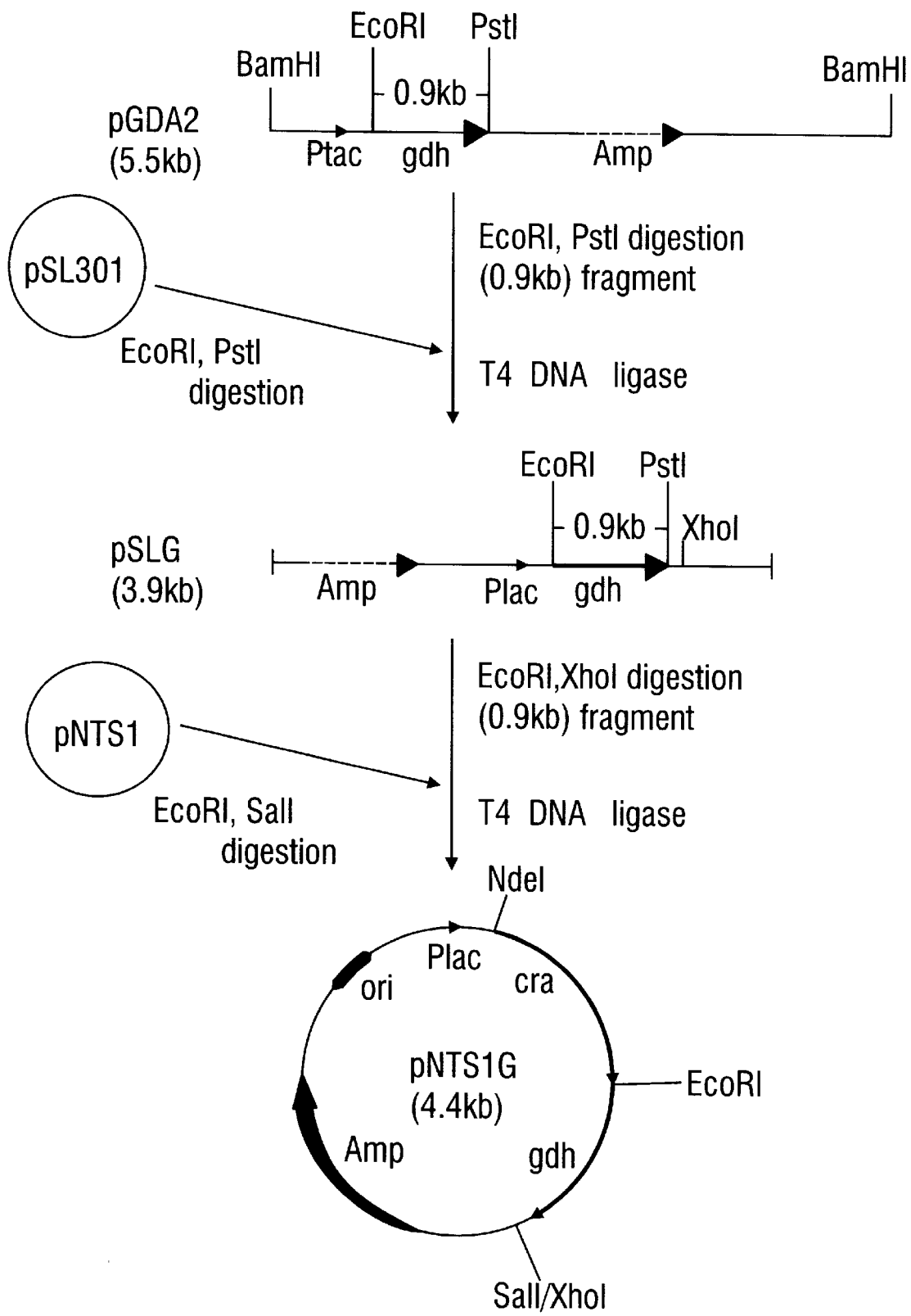
FIG. 2 is a view illustrating a method for constructing a recombinant plasmid pNTS1G.

Hereinafter, the present invention will be described in further detail.

(Purification of CRD Enzyme)

The organism used as a source of the CRD enzyme according to the present invention is not specifically restricted, but can be a yeast of the genus Candida, for example. An especially preferable example is *Candida magnoliae* IFO 0705, which is a microbe originally deposited with Centraalbureau voor Schimmelcultures (CBS; Oosterstraat 1, Postbus 273, NL-3740 A G Baarn, Netherlands) under the number CBS166, and of which isolation and characteristics are described in "The Yeasts, a Taxonomic Study, 3rd ed. (1984) pp. 731. The microbe capable of producing the enzyme according to the present invention can be of a wild strain or a mutant strain. Alternatively, a microbe derived by a genetic technique such as cell fusion or genetic manipulation may also be used. For example, a microbe derived by genetic manipulation which produces the enzyme according to the present invention can be obtained by a method including the steps of: isolating and/or purifying such an enzyme to determine part or all of the amino acid sequence of the enzyme; obtaining a DNA sequence of a DNA coding for the enzyme based on the obtained amino acid sequence; introducing the DNA into another microbe to obtain a recombinant microbe; and culturing the recombinant microbe to obtain the enzyme according to the present invention.

The medium for culturing a microbe for obtaining the enzyme according to the present invention (or an microbe used in the production method of (S)-4-halo-3-hydroxy butyric ester according to the present invention) is not especially restricted as long as it can grow the microbe. For example, a normal liquid nutritious medium containing a carbon source, a nitrogen source, an inorganic salt, an organic nutrient, and the like may be used.

The "microbe culture" as used herein means a microbe body or a liquid culture containing the microbe body, and "its processed product" means a product obtained by extraction and purification as described below, for example.

An enzyme extraction and purification method normally used by those skilled in the art can be used for extracting and purifying an enzyme from the resultant culture. For example, the culture is centrifuged to separate out the microbe bodies, and the resultant microbe bodies are suspended in an appropriate buffer. The microbe bodies in the suspension are destroyed or dissolved by use of a physical technique such as using glass beads or a biochemical technique such as using an enzyme. Solids in the solution are then removed by centrifugation, to obtain a crude enzyme solution. Alternatively, such a crude enzyme solution can be obtained from the culture by a purification method similar to that described above.

The above crude enzyme solution can be further purified by using a method normally used by those skilled in the art, such as ammonium sulfate precipitation, dialysis, and chromatography, alone or in combination. As for the chromatography, various types of chromatography, such as hydrophobic chromatography, ion exchange chromatography, (e.g., DEAE Sepharose), and gel filtration, can be used alone or in combination, to obtain the enzyme according to the present invention.

For example, a CRD enzyme can be isolated from *Candida magnoliae* IFO 0705 in the following manner.

First, the above yeast is cultured in an appropriate medium, and microbe bodies are collected from the resultant culture by centrifugation. The microbe bodies are destroyed by Dyno mill (manufactured by Dyno-Mill), for example, and centrifuged to remove cell debris and thus obtain a cell-free extract. The cell-free extract is then subjected to a processing, such as salting-out (e.g., ammonium sulfate precipitation and sodium phosphate precipitation), solvent precipitation (a protein fractionation precipitation method using acetone, ethanol, or the like), dialysis, gel filtration, ion exchange, column chromatography such as a reverse phase chromatography, and ultrafiltration, alone or in combination, to purify the enzyme. The CRD enzyme activity can be determined by measuring a reduction in the absorption at 340 nm at 30° C., for a 100 mM phosphate buffer (pH 6.5) with 1 mM ethyl 4-chloroacetoacetate as a substrate, 0.1 mM NADPH as a coenzyme, and the enzyme added thereto, or a 200 mM phosphate buffer (pH 7.0) with 0.2 mM ethyl 4-chloroacetoacetate as a substrate and 0.32 mM NADPH as a coenzyme added thereto. Under these reaction conditions, oxidation of 1 $\mu$mol NADPH into NADP in one minute is defined as one unit of enzymatic activity.

The expression that an enzyme is "stable" as used herein means that after being processed at pH 7.0 at 40° C. for 30 minutes the enzyme sustains an activity of 90% or more of that before the processing.

The molecular weight of the enzyme is measured by gel filtration using a column TSK-G3000SW ($\phi$0.75×60 cm; manufactured by Tosoh Corporation). As an eluent, a 0.1M phosphate buffer (pH 7.0) containing 0.1M $Na_2SO_4$ and 0.05% $NaN_3$ is used. The molecular weight of a subunit is determined by performing electrophoresis with 10% SDS-polyacrylamide gel under reducing conditions (reductant: 2 V/V% 2-mercaptoethanol) and calculating from the relative mobility of a standard protein.

For example, a CRD enzyme having an amino acid sequence of SEQ ID NO:1 according to the present invention has physical and chemical properties (1) to (4) of:
(1) action:
acting on ethyl 4-chloroacetoacetate using NADPH as a coenzyme to produce ethyl (S)-4-chloro-3-hydroxybutyrate;
(2) substrate specificity:
exhibiting a strong activity to ethyl 4-chloroacetoacetate while exhibiting substantially no activity to ethyl acetoacetate;
(3) optimal pH: 5.5 to 6.5; and
(4) action optimal temperature: 50° C. to 55° C.

In one embodiment, the carbonyl reductase having the amino acid sequence of SEQ ID NO:1 according to the present invention has additional physical and chemical properties (5) to (7) of:
(5) heat stability: being stable up to about 40° C. when processed at pH 7.0 for 30 minutes;
(6) inhibitor: being inhibited by mercury ions and quercetin; and
(7) molecular weight: about 76,000 in gel filtration analysis and about 32,000 in SDS polyacrylamide electrophoresis analysis.

An enzyme having substantially identical properties as the enzyme according to the present invention may be a natural enzyme or a recombinant enzyme. For example, a recombinant enzyme can be obtained in the following manner: One amino acid or several amino acids in the amino acid sequence of an enzyme derived from *Candida magnoliae* IFO 0705 are substituted, deleted, inserted, or added to produce the recombinant enzyme, and the enzyme activity thereof is measured.

(Preparation of Synthetic Oligonucleotide Probe)

The purified CRD enzyme obtained in the above manner is denatured (e.g., with 8M urea), and then digested with endopeptidase (e.g., lysyl endopeptidase). The amino acid sequence of the resultant peptide fragment is determined by Edman method. A DNA probe is synthesized based on the determined amino acid sequence. Such a probe can be labeled with $^{32}$P, for example.

(Creation of Gene Library)

A chromosomal DNA of a microbe producing the CRD enzyme according to the present invention or cDNA thereof is partially digested with an appropriate restriction enzyme, e.g., Sau3AI. A DNA fragment having an appropriate size (e.g., 23 kb to 20 kb) of the digested product is inserted into a compatible restriction enzyme site of a phage vector. The resultant recombinant phage vector is packaged in vitro and then allows *E. coli* to be infected therewith, to create a gene library.

(Cloning of CRD Enzyme Gene from Gene Library)

The thus-created gene library can be screened for a CRD enzyme gene by a plaque hybridization method using a $^{32}$P labeled synthetic DNAprobe (Science, 196, 180 (1977)). The base sequence analysis of the resultant DNA can be determined by a dideoxy sequencing method, a dideoxy chain termination method, or the like. Such sequence determination can be performed using ABI PRISM Dye Terminator Cycle Sequencing Ready Reaction Kit (manufactured by Perkin Elmer) and ABI 373A DNA Sequencer (manufactured by Applied Biosystems).

The resultant DNA fragment can be amplified by a PCR method or the like and cloned.

(Construction of Recombinant Plasmid Including CRD Enzyme Gene)

A CRD enzyme gene is introduced into a host microbe and expressed therein using a vector DNA. As such a vector DNA, any vector DNA can be used as long as it can express the CRD enzyme gene within an appropriate host microbe. Examples of such a vector DNA include a plasmid vector, a phage vector, and a cosmid vector. A shuttle vector allowing for gene exchange between different host strains may be used. Such a vector DNA may have a control element such as a promoter (e.g., lacUV5 promoter, trp promoter, trc promoter, tac promoter, lpp promoter, tufB promoter, recA promoter, and pL promoter) and an enhancer element operably linked thereto. For example, PUCNT (WO94/03613) and the like may be preferably used. The plasmid pUCNT is preferable since it has insertion sites such as NdeI and EcoRI downstream of a lac promoter.

(Construction of Recombinant Plasmid Including Both CRD Enzyme Gene and Gene of Enzyme Having Ability of Regenerating Coenzyme on which the CRD Enzyme Depends)

As enzymes having the ability of regenerating a coenzyme, hydrogenase, formate dehydrogenase, alcohol dehydrogenase, aldehyde dehydrogenase, glucose-6-phosphate dehydrogenase, glucose dehydrogenase, and the like may be used. Preferably, glucose dehydrogenase is used. More specifically, a *Bacillus megaterium* derived glucose dehydrogenase (hereinafter, abbreviated as GDH) is used.

Plasmid pGDA2 (J. Biol. Chem. (1989), 264, 6381) includes a *Bacillus megaterium* derived GDH gene. A GDH gene fragment is cut out from this plasmid, and inserted into a plasmid including a CRD enzyme gene upstream or downstream of the CRD enzyme gene, to produce a recombinant plasmid having both the CRD enzyme gene and the GDH gene.

(Transformation)

The resultant recombinant plasmid having a CRD enzyme gene or a recombinant plasmid having both a CRD enzyme gene and a GDH gene can be introduced into a host cell by a conventional method. Alternatively, a recombinant plasmid having a CRD enzyme gene and a recombinant plasmid having a GDH gene may be introduced into a host cell simultaneously or at different times, to obtain a transformant strain transformed with these two plasmid.

As such a host cell, a bacterium, a yeast, a thread fungus, a plant cell, an animal cell, and the like may be used. *E. coli* is especially preferably used.

A plasmid can be introduced into a host by a method known in the art, such as a method including the step of mixing a host cell in a competent state and a recombinant plasmid and a method including the step of transfecting a plasmid using a helper plasmid by conjugational transmission.

The plasmid introduced into a host can be autonomically replicated as an episome. Alternatively, all or part of the plasmid may be incorporated in a chromosome and replicated together with the chromosome.

The GDH activity of the transformed cell can be determined by measuring an increase in the absorption at 340 nm at 25° C., for a 1 M tris hydrochloric acid buffer (pH 8.0) with 0.1 M glucose as a substrate, 2 mM NADP as a coenzyme, and the enzyme added thereto.

(Acquisition of Optically Active Alcohol)

Optically active 4-halo-3-hydroxy butyric ester, which is one type of optically active alcohol, is acquired in the following manner, for example.

As a substrate, 4-halo acetoacetic ester represented by the general formula:

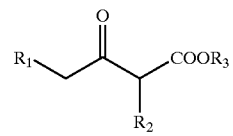

(wherein $R_1$ is a halogen, $R_2$ is a hydrogen, and $R_3$ is a substituted or non-substituted alkyl group or aryl group) may be used. When $R_3$ is an alkyl group, it is, for example, a methyl group, an ethyl group, a propyl group, a butyl group, an isopropyl group, or the like. When $R_3$ is an aryl group, it is, for example, a phenyl group, a tolyl group, or the like. When $R_3$ is a substituted aryl group, it is, for example, a fluorophenyl group, a chlorophenyl group, or the like.

Preferably, $R_1$ is chlorine or bromine, and $R_3$ is an alkyl group having 1 to 4 carbons. More preferably, the substrate is methyl 4-chloroacetoacetate, ethyl 4-chloroacetoacetate, methyl 4-bromoacetoacetate, or ethyl 4-bromoacetoacetate. Alternatively, ethyl 4-iodoacetoacetate, ethyl 4-hydroxyacetoacetate, ethyl 2-chloro-3-oxobutyrate, ethyl 2-methyl-3-oxobutyrate, ethyl 4-azideacetoacetate, and the like may be used as a substrate.

The above 4-halo acetoacetic ester may be prepared by the method disclosed, for example, in Japanese Laid-Open Publication No. 61-146191. For example, the 4-halo acetoacetic ester may be prepared by a method where diketene is used as a starting material and reacted with a halogen to obtain 4-halo acetoacetate halide which is then reacted with alcohol. Alternatively, the 4-halo acetoacetic ester may be prepared by a method where an acetoacetic ester is used as a starting material and the quaternary position thereof is directly halogenated.

The 4-halo acetoacetic ester as a substrate is added to an appropriate solvent together with NADPH as a coenzyme and a culture of the transformant microbe or its processed product and the like, and stirred while pH being adjusted.

This reaction is performed at pH 4 to 10 at a temperature of 10° C. to 70° C. Although the prepared concentration of the substrate is ranging between 0.1% and 90% (w/v), the substrate may be continuously added. The reaction is performed in a batch manner or a continuous manner.

The processed product of a microbe and the like mentioned above refers to a crude extract, cultured microbe bodies, a lyophilized organism, an acetone dried organism, homogenates of such microbe bodies, and the like. Such processed products and the like may be used in the state of being immobilized as they are, that is, as enzymes or microbe bodies, by a known means. The immobilization may be performed by a method known to those skilled in the art (e.g., a crosslinking method, a physical absorption method, and an entrapping method).

In the reaction, the amount of an expensive coenzyme used in the reaction can be greatly reduced by using a general NADPH regeneration system in combination. For example, a method using GDH and glucose which are typical NADPH regeneration systems may be employed. The reaction conditions are as follows although they depend on the enzyme, the microbe or its processed product, the substrate concentration, and the like to be used: the substrate concentration is ranging about 0.1 and 90 wt %, the reaction temperature is 10° C. to 50° C., pH is 5 to 8, and the reaction time is 1 to 36 hours.

The above reaction may be performed using a culture of a transformed microbe or a processed product thereof obtained by introducing both a CRD enzyme gene and a gene of an enzyme (e.g., GDH) having the ability of regenerating coenzyme on which the CRD enzyme gene depends into a host microbe. In this case, additional preparation of an enzyme source required for regeneration of a coenzyme is not necessary, and (S)-4-halo-3-hydroxy butyric ester can be produced at a lower cost.

The 4-halo-3-hydroxy butyric ester produced by the reaction can be purified by a conventional method. For example, the 4-halo-3-hydroxy butyric ester is subjected to centrifugation, filtration and other processings as required in the case where a microbe is used, to remove suspending substances such as microbe bodies. The resultant product is subjected to extraction with an organic solvent such as ethyl acetate and toluene, and dehydrated with a dehydrant such as sodium sulfate. The organic solvent is removed under decompression. The resultant product is then subjected to decompression evaporation, chromatography (e.g., silica gel column chromatography), and the like to be purified.

The quantification of 4-halo-3-hydroxy butyric ester can be performed by gas chromatography. For example, the quantification of ethyl 4-chloro-3-hydroxybutyrate may be performed by chromatography using a glass column (ID 3 mm×1 m) filled with PEG-20M Chromosorb WAWDMCS 10% 80/100 mesh (manufactured by GL Science Co., Ltd.) at 150° C. and detection with FID.

The optical purity of ethyl (S)-4-halo-3-hydroxybutyrate can be measured by HPLC using an optical isolation column CHIRALCEL OB (manufactured by Daicel Chemical Industries, Co., Ltd.)

Thus, as described above, the present invention enables mass production of CRD enzyme. Further, by using this enzyme, an efficient production method of optically active alcohol, such as (S)-4-halo-3-hydroxy butyric ester, is provided.

Hereinafter, the present invention will be described in detail by way of illustrative, but not restrictive, examples.

The details of the manipulation method relating to the recombination DNA technique employed in the examples are described in the following texts.
(I) Molecular Cloning 2nd Edition (Cold Spring Harbor Laboratory Press, 1989)
(II) Current Protocols in Molecular Biology (Greene Publishing Associates and Wiley-Interscience)

EXAMPLE 1
Purification of CRD Enzyme

A CRD enzyme having the ability of reducing 4-halo acetoacetic ester asymmetrically from *Candida magnoliae* IFO 0705 to produce (S)-4-halo-3-hydroxy butyric ester was purified in the following manner so as to move as a single band electrophoretically.

A liquid medium, 8000 ml, of the following composition was prepared, and a 400 ml portion was dispensed into 2000 ml Sakaguchi flasks, and sterilized with steam at 120° C. for 20 minutes.

Composition of Medium

| | |
|---|---|
| Glucose | 5% |
| polypeptone | 0.5% |
| KH2PO4 | 0.2% |
| K2HPO4 | 0.1% |
| MgSO$_4$.7H$_2$O | 0.02% |
| Tap water | |
| pH 6.5 | |

The above medium was inoculated with a culture of *Candida magnoliae* IFO 0705, which had been pre-cultured in the medium, by 5 ml/flask and cultured for three days at 30° C. with agitation. Microbe bodies were collected from the resultant culture by centrifugation and then cleaned twice with saline solution, thereby to obtain 230 g of wet microbe bodies. Among the wet microbe bodies, 180 g was suspended in 360 ml of a 50 mM phosphate buffer (pH 7.0), and then the microbe bodies were destroyed by Dyno mill (manufactured by Dyno-Mill). The destroyed microbe bodies were centrifuged to remove cell debris and thus obtain 760 ml of a cell-free extract. Ammonium sulfate was added to and dissolved in the cell-free extract so as to obtain 40% saturation. The resultant precipitates were removed by centrifugation, and the supernatant was dialyzed with a 10 mM phosphate buffer (pH 7.0) containing 0.1 mM DTT. The resultant product was supplied to a column (500 ml) of DEAE Sephacel (manufactured by Pharmacia Biotech) which had been equilibrated with the same buffer, and the column was washed with the same buffer. Active fractions were collected from the eluted solution which had passed through the column, and NaCl was added to the collected active fractions so as to obtain a final concentration of 4 M. The active fractions were supplied to a column (200 ml) of Phenyl Sepharose CL-4B (manufactured by Pharmacia Biotech) which had been equilibrated with a 10 mM phosphate buffer (pH 7.0) containing 4 M NaCl and 0.1 mM DTT, so as to adsorb enzyme. After the column was washed with the same buffer, the active fractions were eluted using a 10 mM phosphate buffer (pH 7.0) with linear gradient of NaCl (from 4 M to 0 M) and ethylene glycol (from 0% to 50% (w/v)). Those of the active fractions eluted initially were collected and dialyzed over night with a 10 mM phosphate buffer (pH 7.0).

The resultant dialysate was supplied to a column (1 ml) of Mono Q HR 5/5 (FPLC system manufactured by Pharmacia Biotech) which had been equilibrated with a 10 mM phosphate buffer (pH 7.0) containing 0.1 mM DTT, and washed with the same buffer. Active fractions in the washing solution were collected and concentrated to 200 μl by ultrafiltration. The concentrate was then supplied to a column (24 ml) of Superdex 200 HR 10/30 (manufactured by Pharmacia Biotech) which had been equilibrated with 10 mM phosphate buffer (pH 7.0) containing 0.2 M sodium chloride and 0.1 mM DTT, and eluted with the same buffer. Active fractions were collected to obtain a purified enzyme specimen.

EXAMPLE 2
Measurement of Properties of Enzyme

The enzymatic properties of the enzyme obtained in Example 1 were examined.

The enzyme activity was determined by, basically, allowing 3 ml of a reaction solution including 0.2 mM ethyl 4-chloroacetoacetate as a substrate, 0.32 mM NADPH as a coenzyme, and 0.1 ml of an enzyme solution in a 200 mM phosphate buffer (pH 7.0) to react at 30° C. for one minute and measuring a reduction in the absorption at 340 nm.

(1) Action

The enzyme acted on ethyl 4-chloroacetoacetate with NADPH as a coenzyme, to produce ethyl (S)-4-hydroxybutyrate having an optical purity of 99% e. e. or more.

(2) Substrate Specificity

The enzyme according to the present invention was reacted using various carbonyl compounds shown in Table 1 below as a substrate under the same conditions as those used for ethyl 4-chloroacetoacetate. As a result, the enzyme exhibited the substrate specificity as shown in Table 1.

TABLE 1

| Substrate 0.2 mM | Relative activity (%) |
|---|---|
| ethyl 4-chloroacetoacetate | 100 |
| Ethyl acetoacetate | 0 |
| p-nitrobenzaldehyde | 0 |
| o-nitrobenzaldehyde | 0 |
| m-nitrobenzaldehyde | 0 |
| p-chlorobenzaldehyde | 0 |
| o-chlorobenzaldehyde | 0 |
| m-chlorobenzaldehyde | 0 |
| Nicotinaldehyde | 0 |
| isonicotinaldehyde | 0 |
| Benzaldehyde | 0 |
| Glyoxal | 0 |
| Methyl glyoxal | 0 |
| Diacetyl | 19 |
| Chloroacetoaldehyde | 0 |
| Camphor quinone | 0 |
| ethyl 2-chloroacetoacetate | 95 |
| methyl 4-chloroacetoacetate | 11 |
| methyl 2-chloroacetoacetate | 11 |
| octyl 4-chloroacetoacetate | 36 |

(3) Optimal pH

The enzyme activity was measured in a range of pH 5.0 to 8.5 using a phosphate buffer or a tris-hydrochloric acid buffer. As a result, the optimal pH for the action of the enzyme on ethyl (S)-4-chloro-3-hydroxybutyrate was 5.5 to 6.5.

(4) Action Optimal Temperature

The activity of the enzyme according to the present invention was measured using ethyl 4-chloroacetoacetate as a substrate for one minute in a temperature range of 20° C. to 60° C. to obtain an optimal temperature. As a result, the optimal temperature was 50° C. to 55° C.

(5) Heat Stability

After the enzyme according to the present invention was treated at pH 7.0 at 40° C. for 30 minutes, the activity of the enzyme was measured using ethyl 4-chloroacetoacetate as a substrate. As a result, the activity of 90% of that before the treatment remained.

(6) Inhibitor

Various metal ions and inhibitors with respective concentrations shown in Table 2 below were added to the above reaction solution, to measure the activity of ethyl (S)-4-chloro-3-hydroxybutyrate using ethyl 4-chloroacetoacetate as a substrate. As a result, the enzyme according to the present invention was inhibited by quercetin and mercury ions as shown in Table 2.

TABLE 2

| Compound | Concentration of addition (mM) | Relative activity (%) |
|---|---|---|
| Non-added | | 100 |
| Quercetin | 0.01 | 84 |
| | 0.1 | 0 |
| Diphenyl hydantoin | 1 | 84 |
| Dicoumarol | 0.1 | 97 |
| 2,4-dinitrophenol | 0.1 | 86 |
| DTNB | 0.05 | 100 |
| Iodoacetic acid | 1 | 100 |
| NEM | 1 | 105 |
| PMSF | 1 | 93 |
| p-CMB | 1 | 88 |
| EDTA | 1 | 95 |
| Phenylhydrazine | 1 | 97 |
| $SnCl_2$ | 1 | 77 |
| $PbCl_2$ | 1 | 86 |
| $CdCl_2$ | 1 | 91 |
| $CuSO_4$ | 1 | 85 |
| $CoCl_2$ | 1 | 89 |
| $MgCl_2$ | 1 | 83 |
| $ZnSO_4$ | 1 | 97 |
| $HgCl_2$ | 0.1 | 49 |

(7) Molecular Weight

The molecular weight of the enzyme was measured using a TSK-G3000SW column and a 0.1 M phosphate buffer (pH 7.0) containing 0.1 M $Na_2SO_4$ and 0.05% $NaN_3$ as an eluent, and found to be about 76,000. The molecular weight of a subunit of the enzyme was determined by being subjecting it to electrophoresis with 10% SDS-polyacrylamide gel under the presence of 2 v/v% 2-mercaptoethanol and calculating from the relative mobility of a standard protein. As a result, the molecular weight of the subunit of the enzyme was determined to be about 32,000.

(8) Organic Solvent Resistance

An equivalent amount of ethyl acetate or butyl acetate was added to a phosphate buffer (pH 7.0) including the enzyme according to the present invention dissolved therein, shaken at 28° C. for 30 minutes, and then centrifuged. The residual activity of the enzyme in the aqueous phase was measured using ethyl 4-chloroacetoacetate as a substrate. As a result, an activity of 72% in the case of the addition of ethyl acetate and an activity of 85% in the case of the addition of butyl acetate remained.

EXAMPLE 3

Production of Ethyl (S)-4-Chloro-3-hydroxybutyrate Using Enzyme According to the Present Invention A 100 mM phosphate buffer (pH 6.5), 25 ml, containing 50 units of the purified enzyme according to the present invention, 250 mg of ethyl 4-chloroacetoacetate, 1.56 mg of NADP, 280 mg of glucose, and 60 units of glucose dehydrogenase (manufactured by Amano Pharmaceutical Co., Ltd.) was stirred at 30° C. for 24 hours. After reaction, the reaction solution was subjected to extraction with ethyl acetate, and an extract after solvent removal was analyzed. As a result, it was found that ethyl (S)-4-chloro-3-hydroxybutyrate having an optical purity of 99% e.e. or more had been produced at a yield of 98%.

The optical purity of ethyl (S)-4-chloro-3-hydroxybutyrate was measured by HPLC using an optical isolation column, CHIRALCEL OB (manufactured by Daicel Chemical Industries, Co., Ltd.). This chromatography was performed using a mixed solvent of hexane/isopropanol of 9/1 as a mobile phase at a flow rate of the mobile phase of 0.8 ml/min. The detection was conducted by measuring the absorption of 215 nm.

The quantification of ethyl (S)-4-chloro-3-hydroxybutyrate was performed by gas chromatography at 150° C. using a glass column (ID 3 mm×1 m) filled with PEG-20M Chromosorb WAW DMCS 10% 80/100 mesh (manufactured by GL Science Co., Ltd.), and detected by FID.

EXAMPLE 4
Production of Ethyl (S)-4-bromo-3-hydroxybutyrate Using Enzyme According to the Present Invention A 100 mM phosphate buffer (pH 6.5), 2.5 ml, containing 5 units of the purified enzyme according to the present invention, 25 mg of ethyl 4-bromoacetoacetate, 0.16 mg of NADP, 28 mg of glucose, and 6 units of glucose dehydrogenase (manufactured by Amano Pharmaceutical Co., Ltd.) was stirred at 30° C. for 24 hours. After reaction, the reaction solution was subjected to extraction with ethyl acetate, and an extract after solvent removal was analyzed. As a result, it was found that ethyl (S)-4-bromo-3-hydroxybutyrate had been produced at a yield of 43%. The quantification of ethyl 4-bromo-3-hydroxybutyrate was performed in substantially the same manner as that for ethyl 4-chloro-3-hydroxybutyrate in Example 2.

EXAMPLE 5
Production of Methyl (S)-4-chloro-3-hydroxybutyrate Using Enzyme According to the Present Invention Butyl acetate, 2.5 ml, was added to 2.5 ml of 100 mM phosphate buffer (pH 6.5) containing 5 units of the purified enzyme according to the present invention, 25 mg of methyl 4-chloroacetoacetate, 0.16 mg of NADP, 28 mg of glucose, and 6 units of glucose dehydrogenase (manufactured by Amano Pharmaceutical Co., Ltd.), and stirred at 30° C. for 24 hours. After reaction, the reaction solution was subjected to extraction with ethyl acetate, and an extract after solvent removal was analyzed. As a result, it was found that methyl (S)-4-chloro-3-hydroxybutyrate had been produced at a yield of 58%. The quantification of the 4-chloro-3-hydroxy methyl butyrate was performed in substantially the same manner as that for ethyl 4-chloro-3-hydroxybutyrate in Example 2.

EXAMPLE 6
Production of Ethyl (S)-4-chloro-3-hydroxybutyrate Using Enzyme According to the Present Invention; Continuous Addition of Substrate Ethyl 4-chloroacetoacetate, 3.8 g, was continuously added to 50 ml of a 100 mM phosphate buffer (pH 6.5) containing 100 units of the purified enzyme according to the present invention, 1.56 mg of NADP, 4.5 g of glucose, 250 units of glucose dehydrogenase (manufactured by Amano Pharmaceutical Co., Ltd.), and Q.24 g NaCl at a rate of 0.23 g per hour, and stirred at 30° C. for 20 hours while adjusting pH using sodium hydroxide. After reaction, the reaction solution was subjected to extraction with ethyl acetate, and an extract after solvent removal was analyzed. As a result, it was found that ethyl (S)-4-chloro-3-hydroxybutyrate having an optical purity of 100% e.e. had been produced at a yield of 91%. The quantification and the measurement of optical purity of the ethyl 4-chloro-3-hydroxybutyrate were performed in substantially the same manner as that in Example 2.

EXAMPLE 7
Cloning of CRD Enzyme Gene
(Creation of Chromosomal DNA Library)

A chromosomal DNA was extracted from a cultured microbe body of *Candida magnoliae* IFO 0705 in accordance with the method described by Hereford (Cell, 18, 1261 (1979)). The resultant chromosomal DNA was partially digested with Sau3AI, and a DNA fragment having a size of 23 kb to 20 kb of the resultant digest was inserted into BamHI site of EMBL3 phage vector (manufactured by Stratagene). The resultant recombinant phage vector was in vitro packaged using Gigapack II Gold (manufactured by Stratagene), and then allowed *E. coli* NM415 to be infected therewith, so as to create a chromosomal DNA library composed of about 20,000 DNAs.
(Preparation of Synthetic Oligonucleotide Probe)

The purified CRD enzyme obtained as described in Example 1 was denatured under the presence of 8 M urea, and then digested with Achromobacter derived lysyl endopeptidase (manufactured by Wako Pure Chemical Industries, Ltd.). The amino acid sequence of the resultant peptide fragment was determined by the Edman method.

Based on the resultant amino acid sequence, DNA probes having the following sequence were synthesized.

Probe 1:  5'-GCNCAYACNAARAAYGA-3'   (SEQ ID NO:3)
Probe 2:  5'-AAYGTNGARTAYCCNGC-3'   (SEQ ID NO:4)
Probe 3:  5'-CTRGTYCTRCTRCTRTT-3'   (SEQ ID NO:5)

The probes 1, 2, and 3 were labeled with $^{32}$P using Megalabel (manufactured by Takara Shuzo Co., Ltd.), and the labeled probes were used in the following experiments.
(Cloning of CRD Enzyme Gene from Chromosome DNA Library)

The chromosome DNA library created as described above was screened for plaques of phages including a CRD enzyme gene by a plaque hybridization method (Science, 196, 180 (1977)) using the $^{32}$P labeled synthetic DNA probes. As a result, one positive plaque was obtained. Then, a recombinant phage DNA obtained from the positive plaque was double digested with EcoRI and HindIII, and the resultant DNA was analyzed by Southern blotting (J. Mol. Biol., 98, 53 (1975)). As a result, it was found that a digested fragment of about 1.3 kb generated by the double digestion with EcoRI and HindIII had been hybridized with the above synthetic DNA probes. Based on this fact, the DNA fragment of about 1.3 kb was inserted into the EcoRI-HindIII site of plasmid pUC19 (manufactured by Takara Shuzo Co., Ltd.) to constitute recombinant plasmid pUC-HE and selected as a chromosome DNA clone including the CRD enzyme gene. This plasmid was named pUC-HE.
(Determination of Base Sequence)

A variety of restriction enzymes were reacted with the above recombinant plasmid pUC-HE, and digested fragments produced during the reaction were analyzed to create a restriction enzyme cleavage map. Then, various DNA fragments obtained during the analysis were inserted into multi-cloning sites of the plasmid pUC19, to obtain recombinant plasmids. Using these recombinant plasmids, base sequences of the respective inserted fragments were analyzed using ABI PRISM Dye Terminator Cycle Sequencing Ready Reaction Kit (manufactured by Perkin Elmer) and ABI 373A DNA Sequencer (manufactured by Applied Biosystems). As a result, the entire base sequence of the DNA fragment of about 1.3 kb which was expected to include a CRD enzyme gene was determined. FIG. 1 shows the thus-determined base sequence. An amino acid sequence estimated from the base sequence for the structural gene portion of the base sequence is also shown under the corresponding base sequence in FIG. 1. The amino acid sequence was compared with a partial amino acid sequence of a lysyl endopeptidase digested peptide fragment of the purified CRD enzyme. As a result, it was found that the partial amino acid sequence of the purified CRD enzyme exists in the amino acid sequence estimated from the base sequence and completely matches therewith (indicated as an underlined portion in the amino acid sequence in FIG. 1) except for the lack of methionine at the N terminus. The methionine at the N terminus is considered to be removed by modification after protein synthesis.

EXAMPLE 8

Construction of Recombinant Plasmid Including CRD Enzyme Gene

In order to express a CRD enzyme in *E. coli* a recombinant plasmid used for transformation was constructed. First, a double-stranded DNA having an NdeI site added to an initiation codon portion of a structural gene of the CRD enzyme and an EcoRI site added immediately after a termination codon thereof was acquired in the following manner. An N-terminus DNA primer having an NdeI site added to the initiation codon portion of the structural gene of the CRD enzyme and a C-terminus DNA primer having an EcoRI site added immediately after the termination codon of the structural gene of the CRD enzyme were synthesized. The base sequences of these two primers are as follows.

N-terminus DNA primer

```
N-terminus DNA primer                           (SEQ ID NO: 6)
5'-TAGTCGTTAACCATATGGCTAAGAACTTCTCCAAC-3'

C-terminus DNA primer                           (SEQ ID NO: 7)
5'-TCTGAGTTAACGAATTCTTAGGGAAGCGTGTAGCCACCGT-3'
```

5'-TAGTCGTTAACCATATGGCTAAGAACTTCTCC AAC-3' (SEQ ID NO: 6)
C-terminus DNA primer
5'-TCTGAGTTAACGAATTCTTAGGGAAGCGTGTA GCCACCGT-3' (SEQ ID NO: 7)

Using the above two synthetic DNA primers, a double-stranded DNA was synthesized using the plasmid pUC-HE obtained in Example 7 as a template. The resultant DNA fragment was digested with NdeI and EcoRI, and inserted into NdeI and EcoRI sites downstream of a lac promoter of the plasmid pUCNT (WO94/03613), to obtain recombinant plasmid pNTS1.

EXAMPLE 9

Production of Recombinant Plasmid Including Both CRD Enzyme Gene and GDH Gene

Plasmid pGDA2 (J. Biol. Chem. (1989), 264, 6381) was double digested with EcoRI and PstI, to isolate a DNA fragment of about 0.9 kb including a *Bacillus megaterium* derived GDH gene. This DNA fragment was inserted into an EcoRI-PstI site of plasmid pSL301 (manufactured by Invitrogen) to construct recombinant plasmid pSLG. The recombinant plasmid pSLG was then double digested with EcoRI and XhoI, to isolate a DNA fragment of about 0.9 kb including a *Bacillus megaterium* derived GDH gene. This DNA fragment was inserted into an EcoRI-SalI site (located downstream of the CRD gene) of the pNTS1 constructed in Example 8, to obtain recombinant plasmid pNTS1G. The construction method and structure of the pNTS1G are illustrated in FIG. 2.

EXAMPLE 10

Construction of Recombinant *E. coli*

*E. coli* HB101 (manufactured by Takara Shuzo Co., Ltd.) was transformed using the recombinant plasmid pNTS1 obtained in Example 8 and the recombinant plasmid pNTS1G obtained in Example 9, to obtain recombinant *E. coli* HB101 (pNTS1) and HB101 (pNTS1G), respectively. The thus-obtained transformants, *E. coli* HB101 (pNTS1) and HB101(pNTS1G), were deposited with the Ministry of International Trade and Industry, Agency of Industrial Science and Technology, National Institute of Bioscience and Human Technology under the respective deposit numbers FERM BP-5834 and FERM BP-5835 on Feb. 24, 1997.

Further, as in Example 9, plasmid pGDA2 (J. Biol. Chem. (1989), 264, 6381) was double digested with EcoRI and PstI, to isolate a DNA fragment of about 0.9 kb including a *Bacillus megaterium* derived GDH gene. This DNA fragment was inserted into an EcoRI-PstI site of plasmid pSTV28 (manufactured by Takara Shuzo Co., Ltd.) to construct recombinant plasmid pSTVG. The *E. coli* HB101 (pNTS1) which had been made competent in advance by a calcium chloride method was transformed with the PSTVG, to obtain *E. coli* HB101 (pNTS1, pSTVG).

EXAMPLE 11

Expression of CRD Enzyme in Recombinant *E. coli* (Determination of CRD Enzyme Activity in Recombinant *E. coli*

The recombinant *E.coli* HB101 (pNTS1) obtained in Example 10 was cultured in a 2×YT medium containing 50 μg/ml of ampicillin, collected, suspended in a 100 mM phosphate buffer (pH 6.5), and subjected to ultrasonic treatment, to obtain a cell-free extract. The CRD enzyme activity of the cell-free extract was measured in the following manner. That is, 1 mM ethyl4-chloroacetoacetate as a substrate, 0.1 mM NADPH as a coenzyme, and the enzyme were added to a 100 mM phosphate buffer (pH 6.5) for reaction, and a reduction in the absorption at 340 nm was measured at 30° C. In these reaction conditions, oxidation of 1 μmol NADPH into NADP in one minute was defined as one unit of enzymatic activity. The thus-measured CRD enzyme activity in the cell-free extract was represented as a specific activity and compared with that of a transformant using only a vector plasmid. Also, the CRD enzyme activity in a cell-free extract of *Candid magnoliae* IFO 0705 prepared in substantially the same manner as that described in Example 1 was obtained for comparison. The results are shown in Table 3 below. The *E. coli* HB101 (pNTS1) exhibited a definite increase in CRD enzyme activity in comparison with *E.coli* HB101 (pUCNT) which was transformed using only a vector plasmid, and exhibited the activity about 8.5 times as large as that of *Candida magnoliae* IFO 0705.

TABLE 3

| Name of strain | CRD specific activity (U/mg) |
| --- | --- |
| HB101 (pUCNT) | <0.01 |
| HB101 (pNTS1) | 16.0 |
| *Candida magnoliae* IFO 0705 | 1.89 |

(Comparison of N-terminus Sequence)

The amino acid sequence at the N terminus of each of CRD enzymes purified from a cell-free extract obtained in substantially the same manner as that in the above-described expression experiment and from a cell-free extract of the *Candida magnoliae* IFO 0705 was determined over 30 residues by the Edman method. The resultant N-terminus amino acid sequences were compared and found to match completely with each other in this range.

EXAMPLE 12
Simultaneous Expression of CRD Enzyme and GDH in Recombinant *E. coli*

The GDH activity of a cell-free extract obtained by processing the recombinant *E. coli* HB101 (pNTS1G) and *E. coli* HB101 (pNTS1, pSTVG) obtained in Example 10 in a manner as described in Example 11 was measured as follows. That is, 0.1 M glucose as a substrate, 2 mM NADP as a coenzyme, and the enzyme were added to a 1 M tris hydrochloric acid buffer (pH 8.0) for reaction, and an increase in the absorption at 340 nm was measured at 25° C. In these reaction conditions, reduction of 1 μmol NADP into NADPH in one minute was defined as one unit of enzymatic activity. The CRD enzyme activity was also measured as in Example 10. The thus-measured CRD enzyme activity and GDH enzyme activity in the cell-free extract were represented as specific activities and compared with those of *E. coli* HB101 (pNTS1), HB101 (pNTS1, pSTVG) and a transformant HB101(pUCNT) using only a vector. The results are shown in Table 4 below. The *E. coil* HB101 (pNTS1G) and HB101 (pNTS1, pSTVG) exhibited a definite increase in CRD enzyme activity and GDH activity in comparison with *E. coli* HB101 (pUCNT) which was transformed using only a vector plasmid.

TABLE 4

| Name of strain | CRD specific activity (U/mg) | GHD specific activity (U/mg) |
| --- | --- | --- |
| HB101 (pUCNT) | <0.01 | <0.01 |
| HB101 (pNTS1) | 16.0 | <0.01 |
| HB101 (pNTS1G) | 8.03 | 62.6 |
| HB101 (pNTS1, pSTVG) | 13.5 | 1.6 |

EXAMPLE 13
Synthesis of (S)-4-halo-3-hydroxy Butyric Ester from 4-halo Acetoacetic Ester Using Recombinant *E. coli* Having CRD Enzyme Gene Introduced Therein The recombinant *E. coli* HB101 (pNTS1) obtained in Example 10 was inoculated in 100 ml of a 2×YT medium sterilized in a 500 ml Sakaguchi flask, and cultured with agitation at 37° C. for 13 hours. GDH (manufactured by Amano Pharmaceutical Co., Ltd.), 1250 U, 5.5 g of glucose, and 1.6 mg of NADP were added to 50 ml of the resultant culture. The culture was stirred at 30° C. while being adjusted at pH 6.5 with a 5 M sodium hydroxide solution. While stirring, ethyl 4-chloroacetoacetate was added to the culture in 250 mg portions every 15 minutes. In this way, a total of 5 g of ethyl 4-chloroacetoacetate was added and the reaction was performed for five hours. After the reaction, the reaction solution was subjected to extraction using ethyl acetate, and an extract after solvent removal was analyzed. As a result, it was found that ethyl (S)-4-chloro-3-hydroxybutyrate having an optical purity of 100% e.e. had been produced at a yield of 90%.

The quantification of ethyl 4-chloro-3-hydroxybutyrate was performed by gas chromatography using a glass column (ID3 mm×1 m) filled with PEG-20M Chromosorb WAW DMCS 10% 80/100 mesh (manufactured by GL Science Co., Ltd.) at 150° C., and detected by FID.

The optical purity of ethyl (S)-4-chloro-3-hydroxybutyrate was measured by HPLC using an optical isolation column, CHIRALCEL OB (manufactured by Daicel Chemical Industries, Co., Ltd.). This chromatography was performed using a mixed solvent of hexane/isopropanol of 9/1 as a mobile phase at a flow rate of the mobile phase of 0.8 ml/min. The detection was conducted by measuring the absorption of 215 nm.

EXAMPLE 14
Synthesis of (S)-4-halo-3-hydroxy Butyric Ester from 4-halo Acetoacetic Ester Using Recombinant *E. coli* with CRD Enzyme and GDH Expressed Simultaneously The recombinant *E. coli* HB101(pNTS1G) obtained in Example 10 was inoculated in 100 ml of a 2×YT medium sterilized in a 500 ml Sakaguchi flask, and cultured with agitation at 37° C. for 13 hours. Glucose, 5.5 g, and 3.2 mg of NADP were added to 50 ml of the resultant culture. The culture was stirred at 30° C. while being adjusted at pH 6.5 with a 5 M sodium hydroxide solution. While stirring, ethyl 4-chloroacetoacetate was added to the culture in 250 mg portions every 15 minutes. In this way, a total of 5 g of ethyl 4-chloroacetoacetate was added and the reaction was performed for five hours. After the reaction, the reaction solution was subjected to extraction using ethyl acetate, and an extract after solvent removal was analyzed. As a result, it was found that ethyl (S)-4-chloro-3-hydroxybutyrate having an optical purity of 100% e.e. had been produced at a yield of 92%.

The quantification and the measurement of optical purity of the ethyl 4-chloro-3-hydroxybutyrate were performed in substantially the same manner as that in Example 13.

EXAMPLE 15
Synthesis of Ethyl (S)-4-chloro-3-hydroxybutyrate from Ethyl 4-chloroacetoacetate Using Recombinant *E. coli* with CRD Enzyme and GDH Expressed Simultaneously The recombinant *E. coli* HB101(pNTS1G) obtained in Example 10 was inoculated in 100 ml of a 2×YT medium sterilized in a 500 ml Sakaguchi flask, and cultured with agitation at 37° C. for 13 hours. Glucose, 19.2 g, and 2.5 mg of NADP were added to 40 ml of the resultant culture. The culture was stirred at 30° C. while being adjusted at pH 6.5 with a 5 M sodium hydroxide solution. While stirring, a total of 16.1 g of ethyl 4-chloroacetoacetate was continuously added to the culture at a rate of about 2 g per hour. The reaction was performed for 24 hours. After the reaction, the reaction solution was subjected to extraction using ethyl acetate, the solvent was removed under decompression, and the concentrate was purified by silica gel column chromatography, to obtain 15.6 g of ethyl (S)-4-chloro-3-hydroxybutyrate. The optical purity of the ethyl (S)-4-chloro-3-hydroxybutyrate was analyzed by an HPLC method and found to be 100% e.e. 1H-NMR(CDCl3) δ (ppm): 1.33(3H,t), 2.65(2H,d), 3.31(1H,d), 3.60(2H,d), 4.2 (3H,m); Column: Chiralcel OB (0.46×25 cm) manufactured by Daicel Chemical Industries, Co., Ltd.; Column temperature: 0° C.; Eluent: n-hexane/2-propanol of 9/1; Flow rate: 0.8 ml/min.; Detection: 215 nm; Elution time: 19.2 minutes for (S), 17.0 minutes for (R).

EXAMPLE 16
Synthesis of Ethyl (S)-4-chloro-3-hydroxybutyrate from Ethyl 4-chloroacetoacetate Using Recombinant *E. coli* with CRD Enzyme and GDH Expressed Simultaneously The recombinant *E. coli* HB101 (pNTS1G) obtained in Example 10 was inoculated in 100 ml of a 2×YT medium sterilized in a 500 ml Sakaguchi flask, and cultured with agitation at 37° C. for 13 hours. Glucose, 9.6 g, was added to 40 ml of the resultant culture. The culture was stirred at 30° C. while being adjusted at pH 6.5 with a 5 M sodium hydroxide solution. While stirring, a total of 8.1 g of ethyl 4-chloroacetoacetate was continuously added to the culture at a rate of about 2 g per hour. The reaction was performed for a total of 24 hours. After the reaction, the reaction solution was subjected to extraction using ethyl acetate, and after solvent removal, the concentrate was analyzed. As a result, it was found that ethyl (S)-4-chloro-3-hydroxybutyrate with an optical purity of 100% e.e. had been produced at a yield of 96%.

EXAMPLE 17
Synthesis of Ethyl (S)-4-bromo-3-hydroxybutyrate from Ethyl 4-bromoacetoacetate Using Recombinant *E. coli* with CRD Enzyme and GDH Expressed Simultaneously The recombinant *E. coli* HB101(pNTS1G) obtained in Example 10 was inoculated in 100 ml of a 2×YT medium sterilized in a 500 ml Sakaguchi flask, and cultured with agitation at 37° C. for 13 hours. Glucose, 1.3 g, 3.2 mg of NADP, and then 1 g of ethyl 4-bromoacetoacetate were added to 50 ml of the resultant culture. The culture was stirred at 30° C. while being adjusted at pH 6.5 with a 5 M sodium hydroxide solution to allow for reaction for 18 hours. After the reaction, the reaction solution was subjected to extraction using ethyl acetate, the solvent was removed under decompression, and the concentrate was purified by silica gel chromatography, to obtain 900 mg of ethyl (S)-4-bromo-3-hydroxybutyrate. The optical purity of the ethyl (S)-4-bromo-3-hydroxybutyrate was analyzed as follows and found to be 100% e.e. That is, the sample was converted to a carbamate using phenyl isocyanate under the presence of pyridine and the optical purity of the carbamate was measured by an HPLC method. 1H-NMR(CDCl3) δ (ppm): 1.38(3H,t), 2.75(2H,m), 3.28(1H,br), 3.51(2H,m), 4.18(3H,q), 4.25(1H,m); Column: Chiralcel OJ (0.46×25 cm) manufactured by Daicel Chemical Industries, Co., Ltd.; Column temperature: 25° C.; Eluent: n-hexane/2-propanol of 9/1; Flow rate: 0.8 ml/min.; Detection: 254 nm; Elution time: 24.2 minutes for (S), 27.8 minutes for (R).

EXAMPLE 18
Synthesis of Ethyl (S)-4-iodo-3-hydroxybutyrate from Ethyl 4-iodoacetoacetate Using Recombinant *E. coli* with CRD Enzyme and GDH Expressed Simultaneously The recombinant *E. coli* HB101 (pNTS1G) obtained in Example 10 was inoculated in 100 ml of a 2×YT medium sterilized in a 500 ml Sakaguchi flask, and cultured with agitation at 37° C. for 13 hours. Glucose, 0.5 g, 3.2 mg of NADP, and then 0.5 g of ethyl 4-iodoacetoacetate were added to 50 ml of the resultant culture. The culture was stirred at 30° C. while being adjusted at pH 6.5 with a 5 M sodium hydroxide solution to allow for reaction for 72 hours. After the reaction, the reaction solution was subjected to extraction using ethyl acetate, the solvent was removed under decompression, and the concentrate was purified by silica gel column chromatography, to obtain 900 mg of ethyl (S)-4-iodo-3-hydroxybutyrate. The optical purity of the ethyl (S)-4-iodo-3-hydroxybutyrate was analyzed as follows and found to be 91.6% e.e. That is, the sample was heated together with sodium cyanide in dimethyl sulfoxide to obtain ethyl 4-cyano-3-hydroxybutyrate, which was then changed to a benzoic ester using benzoyl chloride under the presence of pyridine. The optical purity of the benzoic ester was measured by an HPLC method. NMR(CDCl3) δ (ppm): 1.28(3H,t), 2.65(2H,d), 3.31(3H,m), 4.00(1H,m), 4.20(2H,q); Column: Chiralpak AS (0.46×25 cm) manufactured by Daicel Chemical Industries, Co., Ltd.; Column temperature: 25° C.; Eluent: n-hexane/ethanol of 95/5; Flow rate: 1 ml/min.; Detection: 254 nm; Elution time: 19.6 minutes for (S), 21.3 minutes for (R).

EXAMPLE 19
Synthesis of Methyl (S)-4-chloro-3-hydroxybutyrate from Methyl 4-chloroacetoacetate Using Recombinant *E. coli* with CRD Enzyme and GDH Expressed Simultaneously The recombinant *E. coli* HB101 (pNTS1G) obtained in Example 10 was inoculated in 100 ml of a 2×YT medium sterilized in a 500 ml Sakaguchi flask, and cultured with agitation at 37° C. for 13 hours. Glucose, 7.2 g, 3.2 mg of NADP, and then 4 g of methyl 4-chloroacetoacetate were added to 50 ml of the resultant culture. The culture was stirred at 30° C. while being adjusted at pH 6.5 with a 5 M sodium hydroxide solution to allow for reaction for 24 hours. After the reaction, the reaction solution was subjected to extraction using ethyl acetate, the solvent was removed under decompression, and the concentrate was purified by silica gel column chromatography, to obtain 3.85 g of methyl (S)-4-chloro-3-hydroxybutyrate. The optical purity of the methyl (S)-4-chloro-3-hydroxybutyrate was analyzed as follows and found to be 100% e.e. That is, the sample was converted to a carbamate using phenyl isocyanate under the presence of pyridine and measuring the optical purity of the carbamate by an HPLC method. 1H-NMR(CDCl3) δ (ppm): 2.65(2H,m), 3.20(1H,br), 3.63(2H,m), 3.73(3H,s), 4.28(1H,m); Column: Chiralcel OJ (0.46×25 cm) manufactured by Daicel Chemical Industries, Co., Ltd.; Column temperature: 25° C.; Eluent: n-hexane/2-propanol of 8/2; Flow rate: 1 ml/min.; Detection: 254 nm; Elution time: 19.2 minutes for (S), 22.6 minutes for (R).

EXAMPLE 20
Synthesis of Ethyl (S)-4-azide-3-hydroxybutyrate from Ethyl 4-azideacetoacetate Using Recombinant *E. coli* with CRD Enzyme and GDH Expressed Simultaneously The recombinant *E. coli* HB101 (pNTS1G) obtained in Example 10 was inoculated in 100 ml of a 2×YT medium sterilized in a 500 ml Sakaguchi flask, and cultured with agitation at 37° C. for 13 hours. Glucose, 3.1 g, 3.2 mg of NADP, and then 2 g of ethyl 4-azideacetoacetate were added to 50 ml of the resultant culture. The culture was stirred at 30° C. while being adjusted at pH 6.5 with a 5 M sodium hydroxide solution to allow for reaction for 72 hours. After the reaction, the reaction solution was subjected to extraction using ethyl acetate, the solvent was removed under decompression, and the concentrate was purified by silica gel column chromatography, to obtain 1.6 g of ethyl (S)-4-azide-3-hydroxybutyrate. The optical purity of the ethyl (S)-4-azide-3-hydroxybutyrate was analyzed by the HPLC method and found to be 90% e.e. 1H-NMR(CDCl3) δ (ppm): 1.25(3H,t), 2.55(2H,d), 3.30–3.35(3H,m), 4.20(3H,m); Column: Chiralcel OB (0.46×25 cm) manufactured by Daicel Chemical Industries, Co., Ltd.; Column temperature: 25° C.; Eluent: n-hexane/2-propanol of 9/1; Flow rate: 1 ml/min.; Detection: 254 nm; Elution time: 16.2 minutes for (S), 19.6 minutes for (R).

EXAMPLE 21
Synthesis of Ethyl (S)-3,4-dihydroxybutyrate from Ethyl 4-hydroxyacetoacetate Using Recombinant *E. coli* with CRD Enzyme and GDH Expressed Simultaneously The recombinant *E. coli* HB101(pNTS1G) obtained in Example 10 was inoculated in 100 ml of a 2×YT medium sterilized in a 500 ml Sakaguchi flask, and cultured with agitation at 37° C. for 13 hours. Glucose, 7.4 g, 3.2 mg of NADP, and then 4 g of ethyl 4-hydroxyacetoacetate were added to 50 ml of the resultant culture. The culture was stirred at 30° C. while being adjusted at pH 6.5 with a 5 M sodium hydroxide solution to allow for reaction for 18 hours. After the reaction, the reaction solution was subjected to extraction using ethyl acetate, the solvent was removed under decompression, and the concentrate was purified by silica gel column chromatography, to obtain 3.2 g of ethyl (S) -3,4-dihydroxybutyrate. The optical purity of the ethyl (S) -3,4-dihydroxybutyrate was analyzed as follows and found to be 100% e.e. The analysis was performed in the following manner. The sample was reacted with sodium cyanide in ethanol at room temperature to obtain 4-cyano-3-hydroxy ethyl butyrate, which was then changed to a benzoic ester using benzoyl chloride under the presence of pyridine. The optical purity of the benzoic ester was measured by the HPLC method. 1NMR(CDCl3) δ (ppm): 1.30 (3H,t), 2.55(2H,m), 3.18(1H,br), 3.55(1H,d), 3.68(1H,d), 4.15(1H,s), 4.20(2H,q); Column: Chiralpak AS (0.46×25 cm) manufactured by Daicel Chemical Industries, Co., Ltd.; Column temperature: 25° C.; Eluent: n-hexane/ethanol of 95/5; Flow rate: 1 ml/min.; Detection: 254 nm; Elution time: 19.6 minutes for (S), 21.3 minutes for (R).

EXAMPLE 22
Synthesis of Ethyl 3-hydroxy-2-methylbutyrate by Reduction of Ethyl 2-methyl-3-oxoacetate Using Recombinant *E. coli* with CRD Enzyme and GDH Expressed Simultaneously The recombinant *E. coli* HB101 (pNTS1G) obtained in Example 10 was inoculated in 100 ml of a 2×YT medium sterilized in a 500 ml Sakaguchi flask, and cultured with agitation at 37° C. for 13 hours. Glucose, 7.5 g, 3.2 mg of NADP, and then 4 g of ethyl 2-methyl-3-oxoacetate were added to 50 ml of the resultant culture. The culture was stirred at 30° C. while being adjusted at pH 6.5 with a 5 M sodium hydroxide solution to allow for reaction for 18 hours. After the reaction, the reaction solution was subjected to extraction using ethyl acetate, the solvent was removed under decompression, and the concentrate was purified by silica gel column chromatography, to obtain 3.5 g of ethyl 3-hydroxy-2-methylbutyrate. The optical purity of the ethyl 3-hydroxy-2-methylbutyrate was analyzed as follows and found to be 91.6% e.e. The analysis was performed in the following manner. The sample was reacted with sodium cyanide in demethyl sulfoxide at room temperature to obtain ethyl 4-cyano-3-hydroxybutyrate, which was then changed to a benzoic ester using benzoyl chloride under the presence of pyridine. The optical purity of the benzoic ester was measured by the HPLC method. 1H-NMR(CDCl3) δ (ppm): 1.17(3H,t), 1.22(2H,t), 1.28(3H,t), 2.46(1H,m), 2.82(1H,br), 3.90(1H,m), 4.18(2H,q).

EXAMPLE 23
Synthesis of Ethyl 2-chloro-3-hydroxybutyrate by Reduction of Ethyl 2-chloro-3-oxoacetate Using Recombinant *E. coli* with CRD Enzyme and GDH Expressed Simultaneously The recombinant *E. coli* HB101 (pNTS1G) obtained in Example 10 was inoculated in 100 ml of a 2×YT medium sterilized in a 500 ml Sakaguchi flask, and cultured with agitation at 37° C. for 13 hours. Glucose, 6.5 g, 3.2 mg of NADP, and then 4 g of ethyl 2-chloro-3-oxoacetate were added to 50 ml of the resultant culture. The culture was stirred at 30° C. while being adjusted at pH 6.5 with a 5 M sodium hydroxide solution to allow for reaction for 18 hours. After the reaction, the reaction solution was subjected to extraction using ethyl acetate, the solvent was removed under decompression, and the concentrate was purified by silica gel column chromatography, to obtain 3.8 g of ethyl 2-chloro-3-hydroxybutyrate. 1H-NMR(CDCl3) δ (ppm): 1.35(6H,m), 2.55(1H,br), 4.15(1H,d), 4.25(1H,nm), 4.30 (2H,q).

Industrial Applicability

By using the novel CRD enzyme, optically active alcohols such as (S) -4-halo-3-hydroxy butyric ester useful as synthetic intermediates for medicines and the like can be efficiently produced.

By cloning the CRD enzyme gene and analyzing the base sequence thereof, a transformant having a high ability of producing the CRD enzyme can be obtained. Also obtained is a transformant having a high ability of producing the CRD enzyme and GDH simultaneously.

By using the above transformants, it is possible to perform synthesis of optically active alcohols such as (S)-4-halo-3-hydroxy butyric ester from carbonyl compounds such as 4-halo acetoacetic ester more efficiently.

---

What is claimed is:

1. A carbonyl reductase protein, wherein:
   the protein catalyzes the conversion of ethyl 4-chloroacetoacetate to (S)-4-chloro-3-hydroxybutyrate using NADPH as a coenzyme;
   the protein has substantially no activity to ethyl acetoacetate;
   the protein has an optimal pH for the conversion of about 5.5 to about 6.5; and
   the protein has an optimal temperature for the conversion of about 50° C. to about 55° C.

2. The protein of claim 1, wherein
   the protein is stable up to about 40° C. at pH 7.0 for 30 minutes;
   the protein is inhibited by mercury ions and quercetin;
   the protein has a molecular weight of about 32,000 as measured by SDS polyacrylamide electrophoresis analysis; and
   the protein has a molecular weight of about 76,000 as measured by gel filtration analysis.

3. The protein of claim 1, further defined as SEQ ID NO:1, SEQ ID NO:1 with one or several amino acids deleted, SEQ ID NO:1 with one or several amino acids substituted, SEQ ID NO:1 with one or several amino acids added, or a catalytically active fragment of SEQ ID NO:1.

4. The protein of claim 1, wherein the protein is a Candida protein.

5. The protein of claim 1, wherein the protein is a *Candida magnoliae* protein.

6. The protein of claim 1, wherein the protein is a *Candida magnoliae* IFO 0705 protein.

7. A method of producing a (S)-4-halo-3-hydroxy butyric ester, the method comprising:
   contacting a 4-halo acetoacetic ester and a carbonyl reductase protein or a cell comprising
   a carbonyl reductase protein; and isolating a (S)-4-halo-3-hydroxy butyric ester; wherein:
   the 4-halo acetoacetic ester is represented by the formula:

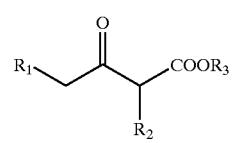

the (S)-4-halo-3-hydroxy butyric ester is represented by the formula:

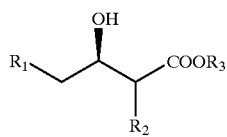

R₁ denotes a halogen atom, R₂ denotes hydrogen, and R₃ denotes substituted or non-substituted alkyl group or aryl group;

the carbonyl reductase protein has substantially no activity to ethyl acetoacetate; and the carbonyl reductase protein catalyzes the conversion of ethyl 4-chloroacetoacetate to (S)-4-chloro-3-hydroxybutyrate using NADPH as a coenzyme.

8. The method of claim 7, wherein:

the halogen atom is chlorine or bromine; and

R₃ is an alkyl group comprising 1 to 4 carbons.

9. The method of claim 7, wherein the 4-halo acetoacetic ester is methyl 4-chloroacetoacetate, ethyl 4-chloroacetoacetate, methyl 4-bromoacetoacetate, or ethyl 4-bromoacetoacetate.

10. The method of claim 7, wherein the cell is a Candida cell.

11. The method of claim 7, wherein the cell is a *Candida magnoliae* cell.

12. The method of claim 7, wherein the cell is a *Candida magnoliae* IFO 0705 cell.

13. The method of claim 7, wherein the cell is transformed with a nucleic acid encoding a carbonyl reductase protein.

14. The method of claim 13, wherein the cell is an *Escherichia coli* cell.

* * * * *

SEQUENCE LISTING

<160> NUMBER OF SEQ ID NOS: 8

<210> SEQ ID NO 1
<211> LENGTH: 283
<212> TYPE: PRT
<213> ORGANISM: Candida magnoliae

<400> SEQUENCE: 1

```
Met Ala Lys Asn Phe Ser Asn Val Glu Tyr Pro Ala Pro Pro Pro Ala
1               5                   10                  15

His Thr Lys Asn Glu Ser Leu Gln Val Leu Asp Leu Phe Lys Leu Asn
            20                  25                  30

Gly Lys Val Ala Ser Ile Thr Gly Ser Ser Ser Gly Ile Gly Tyr Ala
        35                  40                  45

Leu Ala Glu Ala Phe Ala Gln Val Gly Ala Asp Val Ala Ile Trp Tyr
    50                  55                  60

Asn Ser His Asp Ala Thr Gly Lys Ala Glu Ala Leu Ala Lys Lys Tyr
65                  70                  75                  80
```

Gly Val Lys Val Lys Ala Tyr Lys Ala Asn Val Ser Ser Asp Ala
                85                  90                  95

Val Lys Gln Thr Ile Glu Gln Gln Ile Lys Asp Phe Gly His Leu Asp
            100                 105                 110

Ile Val Val Ala Asn Ala Gly Ile Pro Trp Thr Lys Gly Ala Tyr Ile
        115                 120                 125

Asp Gln Asp Asp Asp Lys His Phe Asp Gln Val Val Asp Val Asp Leu
    130                 135                 140

Lys Gly Val Gly Tyr Val Ala Lys His Ala Gly Arg His Phe Arg Glu
145                 150                 155                 160

Arg Phe Glu Lys Glu Gly Lys Lys Gly Ala Leu Val Phe Thr Ala Ser
            165                 170                 175

Met Ser Gly His Ile Val Asn Val Pro Gln Phe Gln Ala Thr Tyr Asn
        180                 185                 190

Ala Ala Lys Ala Gly Val Arg His Phe Ala Lys Ser Leu Ala Val Glu
    195                 200                 205

Phe Ala Pro Phe Ala Arg Val Asn Ser Val Ser Pro Gly Tyr Ile Asn
210                 215                 220

Thr Glu Ile Ser Asp Phe Val Pro Gln Glu Thr Gln Asn Lys Trp Trp
225                 230                 235                 240

Ser Leu Val Pro Leu Gly Arg Gly Gly Glu Thr Ala Glu Leu Val Gly
            245                 250                 255

Ala Tyr Leu Phe Leu Ala Ser Asp Ala Gly Ser Tyr Ala Thr Gly Thr
        260                 265                 270

Asp Ile Ile Val Asp Gly Gly Tyr Thr Leu Pro
    275                 280

<210> SEQ ID NO 2
<211> LENGTH: 852
<212> TYPE: DNA
<213> ORGANISM: Candida magnoliae

<400> SEQUENCE: 2
atggctaaga acttctccaa cgtcgagtac cccgccccgc tccggcccca ccaagaac      60 gagtcgctgc aggtccttga cctgttcaag ctgaatggca aggttgccag catcactggc    120
tcgtccagcg gtattggcta cgctctggct gaggccttcg cgcaggtcgg cgctgacgtc    180
gccatctggt acaacagcca cgacgctact ggcaaggctg aggccctcgc caagaagtac    240
ggcgtcaagg tcaaggccta caaggcgaac gtgagcagct ctgacgccgt gaagcagacg    300
atcgagcagc agatcaagga cttcggccac ctcgacattg tcgtggcgaa cgccggcatt    360
ccctggacga agggtgccta catcgaccag gacgacgaca agcacttcga ccaggtcgtt    420
gacgtcgatc tgaagggtgt tggatacgtc gcgaagcacg ctggccgtca cttccgcgag    480
cgcttcgaga aggagggcaa gaagggcgcc cttgtgttca cggcctccat gtctggccac    540
attgtgaacg tgccccagtt ccaggccacg tacaacgcgg ccaaggctgg cgtgcgccac    600
ttcgcgaagt cgctggccgt cgagttcgcg ccgttcgcgc gcgtgaactc tgtgtcgccg    660
ggctacatca acacggagat ctcggacttc gtgccccagg agacgcagaa caagtggtgg    720
tcgctcgtgc cccttggccg cggcggagag acggccgagc tcgttggcgc ctacctgttc    780
cttgcatctg acgccggctc gtacgccact ggtacggaca tcattgttga cggtggctac    840
acgcttccct aa                                                        852

```
<210> SEQ ID NO 3
<211> LENGTH: 17
<212> TYPE: DNA
<213> ORGANISM: Artificial Sequence
<220> FEATURE:
<223> OTHER INFORMATION: Synthetic Sequence
<221> NAME/KEY: misc_feature
<222> LOCATION: (3)..(3)
<223> OTHER INFORMATION: n = a, c, g, or t
<221> NAME/KEY: misc_feature
<222> LOCATION: (9)..(9)
<223> OTHER INFORMATION: n = a, c, g, or t

<400> SEQUENCE: 3
gcncayacna araayga                                                    17

<210> SEQ ID NO 4
<211> LENGTH: 17
<212> TYPE: DNA
<213> ORGANISM: Artificial Sequence
<220> FEATURE:
<223> OTHER INFORMATION: Synthetic Sequence
<221> NAME/KEY: misc_feature
<222> LOCATION: (6)..(6)
<223> OTHER INFORMATION: n = a, c, g, or t
<221> NAME/KEY: misc_feature
<222> LOCATION: (15)..(15)
<223> OTHER INFORMATION: n = a, c, g, or t

<400> SEQUENCE: 4
aaygtngart ayccngc                                                    17

<210> SEQ ID NO 5
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 5
ctrgtyctrc trctrtt                                                    17

<210> SEQ ID NO 6
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 6
tagtcgttaa ccatatggct aagaacttct ccaac                                35

<210> SEQ ID NO 7
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 7
tctgagttaa cgaattctta gggaagcgtg tagccaccgt                           40

<210> SEQ ID NO 8
<211> LENGTH: 1303
<212> TYPE: DNA
<213> ORGANISM: Candida magnoliae

<400> SEQUENCE: 8
```

-continued

| | | | | | |
|---|---|---|---|---|---|
| aagcttgggg | aaccgacgtc | cccgccctcg | tacatgcagt | gcatacagca | ttgcccaaac | 60 |
| cccacattgt | gcccccaccc | ccccgcggat | tccgtaacta | tataaaggcc | gccagtgccg | 120 |
| actatggacc | atcatcccga | aatcaccaag | aactaacaat | ggctaagaac | ttctccaacg | 180 |
| tcgagtaccc | cgccccgcct | ccggcccaca | ccaagaacga | gtcgctgcag | gtccttgacc | 240 |
| tgttcaagct | gaatggcaag | gttgccagca | tcactggctc | gtccagcggt | attggctacg | 300 |
| ctctggctga | ggccttcgcg | caggtcggcg | ctgacgtcgc | catctggtac | aacagccacg | 360 |
| acgctactgg | caaggctgag | gccctcgcca | agaagtacgg | cgtcaaggtc | aaggcctaca | 420 |
| aggcgaacgt | gagcagctct | gacgccgtga | agcagacgat | cgagcagcag | atcaaggact | 480 |
| tcggccacct | cgacattgtc | gtggcgaacg | ccggcattcc | ctggacgaag | ggtgcctaca | 540 |
| tcgaccagga | cgacgacaag | cacttcgacc | aggtcgttga | cgtcgatctg | aagggtgttg | 600 |
| gatacgtcgc | gaagcacgct | ggccgtcact | tccgcgagcg | cttcgagaag | gagggcaaga | 660 |
| agggcgccct | tgtgttcacg | gcctccatgt | ctggccacat | tgtgaacgtg | ccccagttcc | 720 |
| aggccacgta | caacgcggcc | aaggctggcg | tgcgccactt | cgcgaagtcg | ctggccgtcg | 780 |
| agttcgcgcc | gttcgcgcgc | gtgaactctg | tgtcgccggg | ctacatcaac | acggagatct | 840 |
| cggacttcgt | gccccaggag | acgcagaaca | agtggtggtc | gctcgtgccc | cttggccgcg | 900 |
| gcggagagac | ggccgagctc | gttggcgcct | acctgttcct | tgcatctgac | gccggctcgt | 960 |
| acgccactgg | tacggacatc | attgttgacg | gtggctacac | gcttccctaa | gcggcgtgcc | 1020 |
| gaaaacatag | agctatctat | ataaccataa | tgatgcgcat | attatgatct | actactttga | 1080 |
| cttcgatcgg | aacttaggaa | cgataagggt | ggaatgcgtg | aaagcgtgca | tgctgcagag | 1140 |
| cggtgtaatc | ggcagggctg | tagggtgcct | gaggcggcgg | gccagcagtg | catgtaaccg | 1200 |
| gagctgaagc | ggaggcacac | attgcgatgc | agcgaagcac | ggccgccaga | actctttgag | 1260 |
| aacaagcgcg | gccctcgact | atgcagcggc | aacaagcgaa | ttc | | 1303 |